United States Patent [19]

Sherwin

[11] 4,124,484

[45] Nov. 7, 1978

[54] DEVELOPER COMPOSITION AND PROCESS FOR PENETRANT INSPECTION

[76] Inventor: Amos G. Sherwin, 8330 Gainford St., Downey, Calif. 90240

[21] Appl. No.: 872,483

[22] Filed: Jan. 26, 1978

[51] Int. Cl.$^2$ ............... C09K 11/06; G01N 19/08; C09K 3/00
[52] U.S. Cl. .................. 252/301.19; 73/104; 250/302; 252/408
[58] Field of Search .............. 250/302; 73/104; 252/301.19, 408

[56] References Cited

U.S. PATENT DOCUMENTS

| | | | |
|---|---|---|---|
| 3,117,227 | 1/1964 | Pollack | 250/302 |
| 3,715,227 | 2/1973 | Alburger | 252/301.19 X |
| 3,803,051 | 4/1974 | Molina | 252/408 |
| 3,939,092 | 2/1976 | Molina | 252/301.19 |
| 4,000,422 | 12/1976 | Kuzmina et al. | 250/302 |

*Primary Examiner*—F.C. Edmundson

[57] ABSTRACT

Dry developer composition in powder form and process for using same in the inspection of metal surfaces for cracks and defects open to the surface by the penetrant process. The powder composition of this invention has special significance in providing easier to see flaw indications when used with the fluorescent penetrant method of inspection.

2 Claims, No Drawings

DEVELOPER COMPOSITION AND PROCESS FOR PENETRANT INSPECTION

This invention is an improvement of the fluorescent penetrant process in which a liquid containing fluorescent dye is applied to a surface, allowed to dwell while it migrates into surface openings such as cracks, and is then removed from the surface, leaving behind liquid which has migrated into surface openings. Whereupon, typically, a developing agent is applied to bring back to the surface the dyestuff containing liquid which has migrated into surface openings so it may be visually observed under ultra-violet light as a location of a surface discontinuity. The developer is normally a powder and is applied either as a dry powder, a powder suspended in a volatile liquid such as alcohol or dissolved or suspended in water.

The developer has two functions in the penetrant process: it brings flaw trapped penetrant liquid back to the surface and it enhances the brightness or visibility of the indications. As previously mentioned, there are three basic types of developers: dry powder, volatile solvent carrier and water carrier. The dry powder and volatile solvent developers are normally favored for highly critical inspections. Ease of application is an advantage of the dry powder over the volatile solvent carrier developer. In addition, the dry powder does not accentuate background problems associated with rough surfaces. The dry powder developer is relied on by manufacturers of turbine engines for these reasons. The dry powder developer may be applied by different means such as placing a basket of parts in a dusting chamber, dusting from a powder bulb, sprinkling, using a soft bristle brush or by immersing the parts into a container of the powder.

Dry powder developers have been used for many years and have been mentioned in several patents including U.S. Pat. No. 2,806,959 which discloses the use of powdered silica and a powdered silica talc mixture. U.S. Pat. No. 2,848,421 offers a variation using silica aerogel and talc. U.S. Pat. No. 2,420,646 discloses use of diatomaceous earth or talc. U.S. Pat. No. 2,920,203 discusses using talc and magnesium carbonate. U.S. Pat. No. 3,117,227 discloses the combination of diatomaceous earth and silica aerogel. U.S. Pat. No. 3,803,051 discloses the use of a mixture of alumina, silica, talc and titanium dioxide and attributes certain advantages to titanium dioxide.

All of these prior disclosures rely on talc or diatomaceous earth as a principal functioning ingredient. My invention replaces talc with aluminum benzoate. Talc, which is magnesium silicate, as mentioned in Patent 3803051, when applied to a metal surface provides an almost invisible film deposit of fine particles which, in turn, provides a capillary path by which the trapped fluorescent penetrant liquid returns to the surface. Aluminum benzoate also provides an adhering microscopic film of powder but the resultant film is heavier and the capillary path is more effective.

Brightness is essential for the detection of microscopic surface flaws by the fluorescent penetrant process. The technician examines the surface visually in a darkened area with ultra-violet light. Indications appear as glowing marks. Normally, the flaw marks glow in the yellow-green spectrum. Incipient cracks may appear as two or three glowing pin points in a line. Whether or not the technician sees these glowing pin points depends, in part, on their intensity or brightness. The brighter the indications, the more reliable will be the inspection.

Indication brightness is a function of both the penetrant and the developer. Brightness of the penetrant, itself, is a product of the type, quantity and mixture of dyestuffs used and their solvency in the carrier liquid. Ultra-violet light excitation of the dissolved dye results in visibility of the liquid to the human eye. The greater the quantity of excitement energy acting on the dissolved fluorescent dyestuff in the liquid, the more brilliant or visible the fluorescent flaw-mark. Ultra-violet light energy absorbed by the liquid is re-radiated in the visible spectrum. Only a portion of the ultra-violet light energy directed on the liquid is absorbed and converted to the visible spectrum, as a percentage of energy passes through the liquid to the underlying surface where it is either absorbed by the surface and converted to a non-responsive energy such as heat or sent back to the liquid as refracted ultra-violet light energy or other wave energy to further excite the dissolved fluorescent dyestuff and increase the brightness or intensity of the liquid or glowing flaw-marks.

The powder developer acts as the underlying surface. A powder which retransmits the most energy back to the liquid would be preferred as a developer. Examining powders normally used in the penetrant process and comparing them to the powder which is the subject of my invention under "black light" or ultra-violet light, it was found that titanium dioxide, talc, aluminum silicate and fumed silica appear to be gray, lavender shade and very dull. On the other hand, aluminum benzoate and magnesium carbonate appear to be white-yellow with scattered traces of lavender in shade.

Both characteristics discussed, leaving a clinging microscopic film of powder on the surface and returning wave energy to the liquid, are essential. For example, while titanium dioxide leaves a light coating on the metal surface after the part has been immersed, its appearance under ultra-violet light is gray and dull and flaw marks produced by titanium dioxide acting alone lack brilliance. On the other hand, magnesium carbonate, while it responds to ultra-violet light with a white-yellow shade, does not leave a clinging film and flaw-marks produced are weak.

The effectiveness of aluminum benzoate as a powder developer is apparent when compared to talc and other typical materials such as calcium carbonate, magnesium oxide, magnesium carbonate, aluminum oxide and aluminum silicate, on test pieces with fine or microscopic cracks and pores. A very small flaw has a minimum quantity of entrapped penetrant liquid to migrate back to the surface to be perceived. In inspecting for such flaws, aluminum benzoate yields more readily visible or detectable marks than other powders now employed. The use of aluminum benzoate will have special significance for industries concerned with the need to detect extremely small flaws such as turbine engine manufacturers where the failure of a rotating part may result in a catastrophic accident.

Aluminum benzoate may be used full strength, without mixing with other powders. As a matter of economy, it can be mixed with talc, alumina calcium carbonate, magnesium carbonate, magnesium oxide and other nonreactive powders. An effective mixture and one that is economical consists of one-third talc, one-third aluminum benzoate and one-third fumed silica by weight. The Cabot Corporation is a source of fumed silica. My favorite mixture is two parts by weight of aluminum benzoate and one part of fumed silica offered by The Cabot Corporation under the tradename Cab-O-Sil HS-5. The use of fumed silica adds a certain fluffiness to the mixture and facilitates the application of the mixture to surfaces.

My dry developer composition is employed in the fluorescent penetrant inspection process as described previously in this disclosure. The dry powder developer composition is applied to the surface after fluorescent penetrant has been removed from the surface and when the surface is dry for the purpose of increasing the visibility of fluorescent indications made as a result of deposits of fluorescent penetrant retained in surface cracks and similar surface discontinuities.

The developer composition may be applied to the surface of the test specimen in many different ways. It may be applied by sprinkling or dusting the powder developer onto the surface, flowing the powder over the surface, dipping the test specimen into the powder, placing the specimen in a dust chamber and blowing the powder over the surfaces with mild air circulation and by other methods.

The fluorescent penetrant composition may be of several different types including water-washable, non-water-washable and solvent removeable. Suitable fluorescent penetrants are commercially available from the Magnaflux Corporation, Chicago; The Met-L-Chek Company, Santa Monica, California; and Sherwin Incorporated, Los Angeles and other companies.

I claim:

1. A dry powder developer composition for inspection of surfaces by the fluorescent penetrant method which composition consists of 30% or more by weight of aluminum benzoate powder with the aluminum benzoate powder in finely divided form having a particle size of less than 2 microns.

2. A flourescent penetrant process which utilizes a developer composition as described in claim 1 to increase the visibility of flaw indications.

* * * * *